United States Patent [19]

Chen et al.

[11] Patent Number: 4,844,242

[45] Date of Patent: Jul. 4, 1989

[54] CORNEA RETAINER

[75] Inventors: Chung-Ho Chen; Sumi C. Chen, both of Phoenix, Md.

[73] Assignee: The Johns Hopkins University, Baltimore, Md.

[21] Appl. No.: 92,322

[22] Filed: Sep. 2, 1987

[51] Int. Cl.[4] ............................................. B65D 81/22
[52] U.S. Cl. ..................................... 206/5.1; 206/438
[58] Field of Search ............... 206/5.1, 438, 205, 570, 206/210

[56] References Cited

U.S. PATENT DOCUMENTS

| 3,770,113 | 11/1973 | Thomas | 206/5.1 |
| 3,822,780 | 7/1974 | Ulmer et al. | 206/5.1 |
| 4,009,777 | 3/1977 | Thomas | 206/5.1 |
| 4,257,521 | 3/1981 | Poler | 206/5.1 |
| 4,396,583 | 8/1983 | Le Boeuf | 206/5.1 |
| 4,423,809 | 1/1984 | Mazzocco | 206/5.1 |
| 4,697,697 | 10/1987 | Graham et al. | 206/5.1 |
| 4,750,610 | 6/1988 | Ryder | 206/5.1 |

Primary Examiner—Joseph Man-Fu Moy
Attorney, Agent, or Firm—Cushman, Darby & Cushman

[57] ABSTRACT

A device for storing isolated donor corneas comprising a medium container for containing corneal storage medium, a cap which co-acts with the medium container to form an airtight seal, and a cornea retaining means attached to the cap for retaining a cornea suspended within the medium container and for preventing the retained cornea from a contacting inner surfaces of the container and cap.

8 Claims, 2 Drawing Sheets

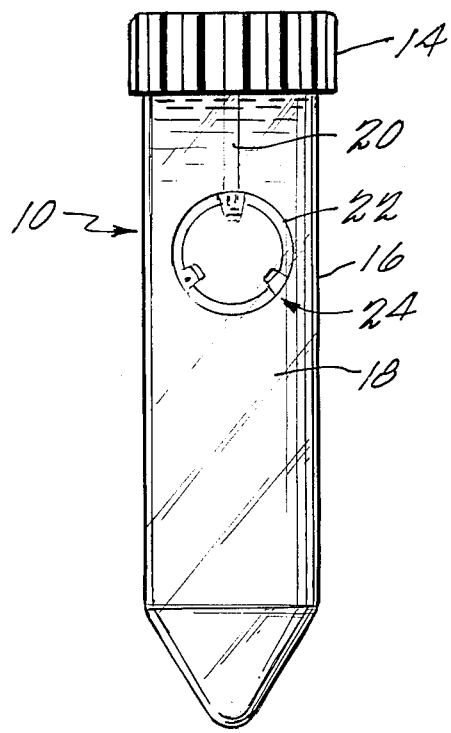
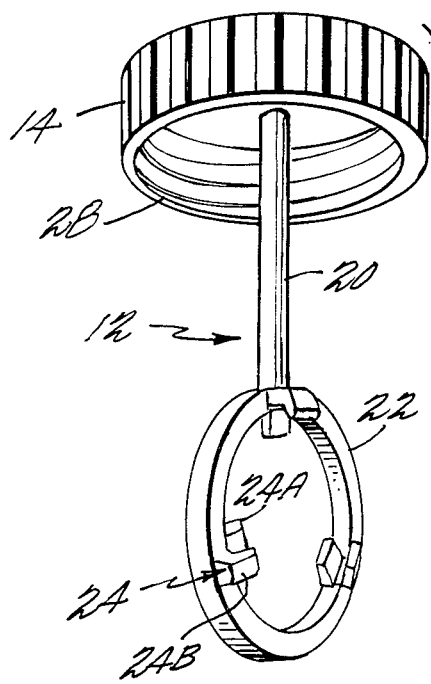
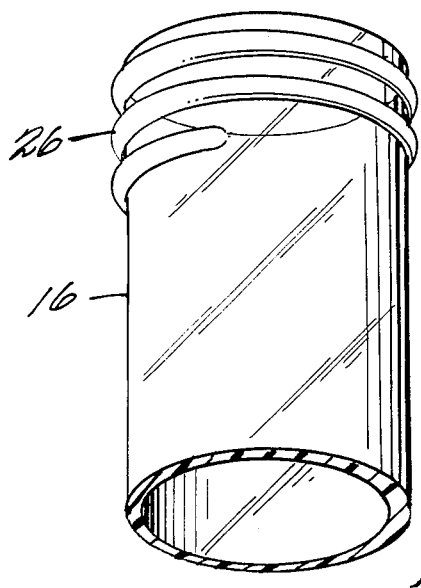
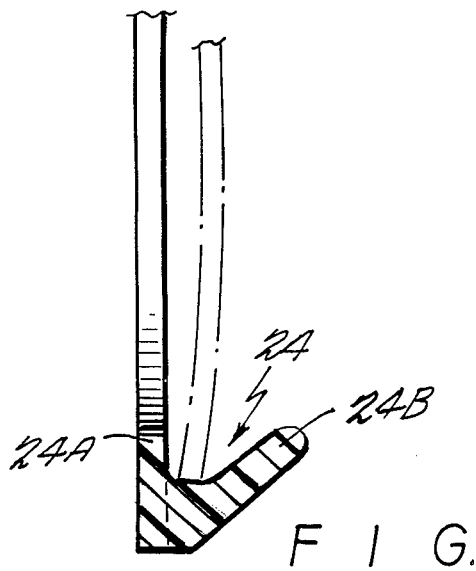

CORNEA RETAINER

BACKGROUND OF THE INVENTION

1. TECHNICAL FIELD

The present invention relates, in general, to a cornea storage device and, in particular, to a cornea retainer which holds isolated donor corneas in a specific orientation during storage.

2. BACKGROUND INFORMATION

At present, penetrating keratoplasty for restoring sight in patients with cornea opacity is highly successful. However, the quantity of surgical-quality donor corneas is in short supply. The number of available corneas is determined by a combination of two factors: (1) the length of time between the death of the donor and the preservation of the cornea, and (2) the length of time that the donor cornea is stored. Presently, procurement of donor corneas no more than 12 hours after death and storage for no more than 72 hours constitute the guidelines for the distribution of donor tissues for transplant. Donor corneas with a preservation time of up to 96 hours are used on an emergency basis.

The development of methods for extending the time donor corneas may be stored has significant clinical implications as well as marketing potential. Extending corneal preservation time increases the quantity of tissues available for transplant, provides surgeons flexibility in performing operations, improves scheduling of elective surgery, and affords more cost efficient use of operating rooms. Patients benefit from enhanced physiological quality of donor corneal tissue.

Presently, isolated human donor corneas are stored in vials containing Medium 199 supplemented with 5% dextran or 2% chondroitin sulfate. An isolated cornea stored in this manner may settle to the bottom of the storage vial with the endothelium-side facing up or down. Under these storage conditions, the medium immediately surrounding the cornea may contain elevated levels of metabolic wastes and insufficient levels of corneal nutrients. When the endothelium faces the bottom of the storage vial, the problems of waste accumulation and nutrient depletion are enhanced. The metabolic activity (an indicator of tissue viability) of corneas subjected to these storage conditions decreases rapidly.

In addition to the deleterious chemical environment surrounding corneas stored according to current protocols, the present storage method also subjects donor tissue to adverse physical conditions. The surface of the corneal tissue is easily disrupted by excessive contact with the inside surface of the storage container. In addition, the retrieval of corneas which have settled to the bottom of storage vials is difficult as only an edge of 2 or 3 mm may contact the forceps without damaging the tissue.

SUMMARY OF THE INVENTION

It is a general object of the invention to obviate or minimize the objections to prior art methods of storing isolated corneas.

It is a particular object of the invention to provide a device which extends the viability of isolated corneas by facilitating removal of metabolic wastes from the medium immediately surrounding the stored tissue and increasing access of stored tissues to nutrients through diffusion.

It is another object of the invention to provide a device which affords the safe and easy retrieval of the stored corneas.

It is a further object of the invention to provide a device which protects the endothelial monolayer of isolated corneas during shipment.

It is a another object of the invention to provide a device which enables the viability of the donor cornea to be assessed, prior to corneal transplantation, by nuclear magnetic resonance spectroscopy, slit-lamp microscopy, and specular microscopy.

Further objects and advantages of the present invention will be apparent from the following detailed description of species thereof taken in connection with the accompanying drawings.

The foregoing objects of the invention are achieved by attaching to a cap, which cap co-acts with an opening of a medium container to form an airtight seal, a means for retaining a cornea suspended within the medium container and for preventing the retained cornea from contacting inner surfaces of the container and cap. When the cap is secured to the container, the thus retained cornea is completely submerged in storage medium present in the container.

BRIEF DESCRIPTION OF THE DRAWINGS

Referring to the drawings:

FIG. 1 is a side elevation of one exemplary embodiment of the instant invention.

FIG. 2 is an enlarged exploded perspective of the exemplary embodiment shown in FIG. 1.

FIG. 4 is an enlarged fragmentary sectional view taken on line 3,3 of FIG. 1.

DESCRIPTION OF THE PREFERRED EMBODIMENT

Figure 3:
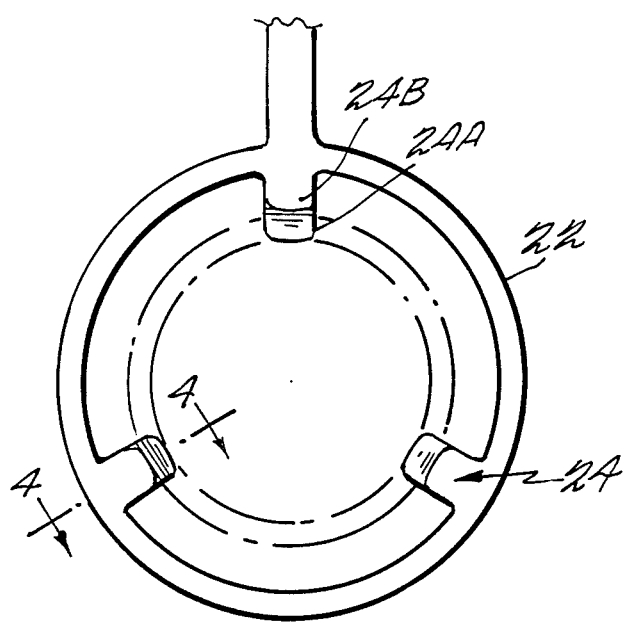
FIG. 3 is an enlarged fragmentary view of the lower portion of the cornea retaining means.

Referring now to the drawings wherein all like numerals indicate like parts, the numeral 10 indicates a cornea storage device and the numeral 12 indicates a cornea retainer of the present invention. In FIG. 1 is shown cap 14 which cap securely attaches to medium container 16 so that an airtight seal is formed. Spillage, evaporation and contamination of corneal storage medium 18 in container 16 are thus prevented. Cap 14 is formed from any suitable rigid polymer and is, advantageously, fitted with a polymer gasket lining. Medium container 16 is comprised of either glass or a rigid polymer, preferably, a polycarbonate polymer of a transparency which allows viewing of the stored cornea.

Medium container 16 may take various forms including that of a conical tube, as shown in FIG. 1, or a cylindrical, flat-bottom bottle or vial having a diameter of, advantageously, 2.5–4.0 cm. The length of medium container 16 is, advantageously, 6.0–8.5 cm. When it is desirable to evaluate, by a nuclear magnetic resonance spectrometer (NMR), the quality of the stored cornea, it is advantageous that medium container 16 have a diameter of approximately 2.5–2.8 cm.

Attached to cap 14 is an upper end of shaft 20. To a lower end of shaft 20 is secured support ring 22. Shaft 20 is of such length and corneal storage medium 18 is of such volume that when cap 14 is secured to container 16, ring 22 is completely covered by storage medium 18; shaft 20 is, advantageously, of such length that ring 22 is positioned at a point approximately one third of the distance from the top of medium container 16 to the bottom. Ring 22 and shaft 20 are comprised, advantageously, of polyethylene. When viability of the donor cornea is to be evaluated by nuclear magnetic resonance spectroscopy, it is desirable that ring 22 and shaft 20 be comprised of phosphorus- and halogen-free polymers or glass.

In a preferred embodiment, three retaining lugs 24 are formed on ring 22. Retaining lugs 24 are, preferably, evenly disposed around ring 22. As will be apparent to those skilled in the art more or less than three retaining lugs can be used.

In FIG. 2 is shown an enlarged view of ring 22. Ring 22 is of sufficient diameter, advantageously, from 1.55 to 1.75 cm, to accommodate isolated corneas of different sizes. Donor corneas may also be trimmed to fit ring 22. Isolated corneas are retained in ring 22 by retaining lugs 24. Corneas thus retained are prevented from contacting the inside walls of medium container 16. Also shown in FIG. 2 are upper external threads 26 formed on medium container 16, which threads co-act with internal threads 28 formed within cap 14 to form an airtight seal.

In FIG. 3 are shown retaining lugs 24. Each retaining lug is comprised of two members, a first member 24A and a second member 24B. Retaining lugs 24 are of sufficient length to retain isolated corneas within ring 22. Retaining lug member 24A is, advantageously, 3-3.5 mm in length and retaining lug member 24B, is advantageously, 4-4.5 mm in length.

In FIG. 4 are shown retaining lugs 24 depending from ring 22. Retaining lug member 24A is, preferably, in the plane of ring 22 and retaining lug member 24B is angularly, advantageously, 55°-60°, disposed with respect to the plane of ring 22. Retaining lug members 24A and 24B form a curved track, advantageously, 0.7-0.8 mm in width, on the inner side of the ring 22. The track helps hold the cornea in place in ring 22. Ring 22 and lugs 24 are smooth without sharp edges and points.

Figure 5:
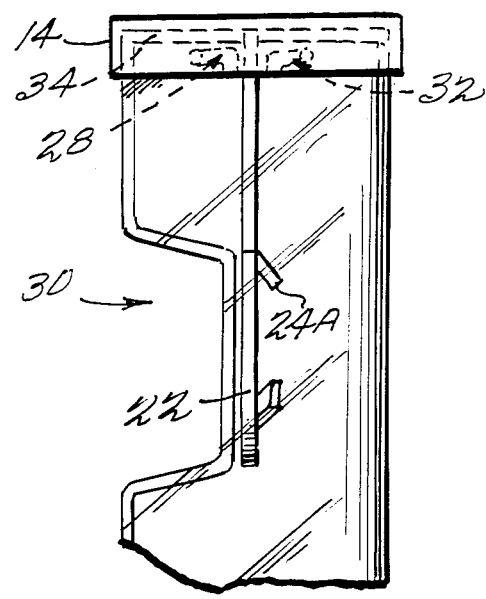
FIG. 5 is a side elevation of a medium container provided with a window for microscopic viewing.
Figure 6:
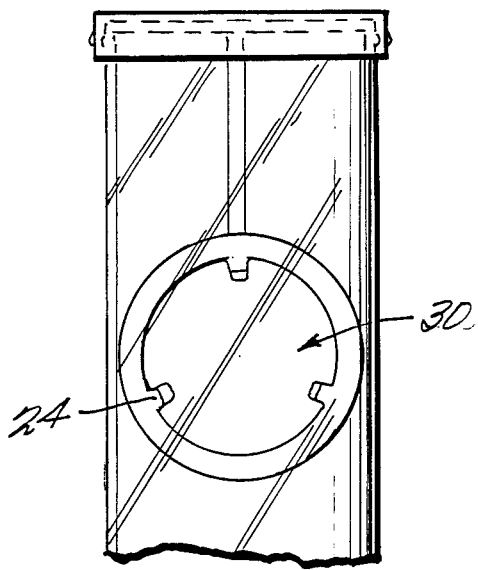
FIG. 6 is a front elevation of the window of the medium container shown in FIG. 5.
Figure 7:
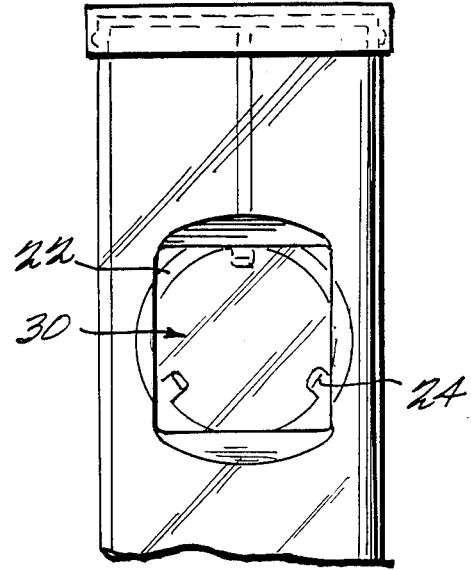
FIG. 7 is a modified form of the window of a medium container shown in FIGS. 5 and 6.

In FIGS. 5-7 is shown another embodiment of the invention wherein medium container 16 is provided with window 30 for examining and photographing, with a slit-lamp and/or specular microscope, the stored donor cornea prior to transplantation. Window 30 is a flat surface, parallel to the walls of medium container 16. Window 30 is, preferably, 0.1-0.3 cm from the center of medium container 16. Window 30 is either a circular surface, as shown in FIG. 6, (when medium container 16 has a large diameter), advantageously, 1.5-2.0 cm in diameter, or a partial circular surface with straight vertical edges as shown in FIG. 7. (when medium container 16 has a small diameter), advantageously, 1.5-2.0 cm in diagonal length. The outer opening of window 30 is, advantageously, greater than that of window 30 so that a microscope objective lens can be accommodated.

When medium container 16 is equipped with window 30, cap 14 is of a twist-closing type or snap-type. When cap 14 is of a twist-closing type, medium container 16 and cap 14 are provided with bayonet slot and connection 32 as shown in FIG. 5. When medium container 16 and cap 14 are co-acted, the donor cornea held in ring 22 is parallel with window 30. Medium container 16 and twist-closing cap 14 co-act to form an airtight seal. Cap 14 is, preferably, fitted with polymer gasket lining 34.

The above-described means for retaining isolated donor corneas permits the simple and safe removal of stored corneas from storage medium. In addition, the orientation of the stored tissue in the storage medium facilitates the removal of metabolic wastes from the medium immediately surrounding the corneal tissue and increases the access of stored tissue to nutrients. When stored for 2 days in the above-described manner, the metabolic activity of donor corneas with a death-to-procurement of 15 hours is comparable to that of corneas with death-to-procurement of 12 hours and a 3-day-storage in the conventional manner. The retention of corneal viability with such an extension of death-to-procurement time is estimated to increase the number of donor corneas available for penetrating keratoplasty by 25%.

Finally, the above-described means for retaining isolated donor corneas prevents the loss of endothelial cells from the donor cornea during shipment. The endothelial monolayer functions as a tissue barrier which mediates the removal of metabolic wastes and the uptake of nutrients. Without the endothelium, the cornea will swell and lose its transparency. Transparency of the cornea is essential for transmission of light to the retina in the visual process.

While the present invention has been illustrated by detailed descriptions of a preferred embodiments thereof, it will be obvious to those skilled in the art that changes in form and detail may be made therein without departing from the true scope of the invention as set forth in the appended claims.

What is claimed is:

1. A cornea storage device comprising:
   (a) a medium container, having an opening at the top thereof, for containing corneal storage medium;
   (b) a cap which co-acts with said opening of said medium container to form an airtight seal; and
   (c) a means for retaining a cornea suspended within said medium container and for preventing the retained cornea from contacting inner surfaces of said medium container and cap, said retaining means comprising a shaft attached at one end to the interior of said cap and adapted to extend downwardly into said container a ring recured to the lower end of said shaft, and spaced from the inner surfaces of the container, and a plurality of retaining lugs formed on said ring, and extending outwardly therefrom so as to provide a curved track to receive and hold said cornea, the orientation of cornea stored in the container facilitating the removal of metabolic wastes from the medium immediately surrounding the cornea and increasing the access of the stored cornea to nutrients.

2. The cornea storage device according to claim 1 wherein said medium container is provided with a window for microscopically viewing said cornea.

3. The cornea storage device according to claim 1 wherein said medium container is formed from a phosphorous and halogen-free polymer or glass so that said cornea can be evaluated with NMR spectroscopy.

4. The cornea storage device according to claim 1 wherein the inner diameter of said ring is in the range of 1.5 to 1.75 cm.

5. The cornea storage device according to claim 1 wherein said plurality of retaining lugs are evenly disposed about said ring.

6. The cornea storage device according to claim 1 wherein said plurality of retaining lugs are in the range of 3 to 4.5 mm in length.

7. A device according to claim 1 including cornea storage medium in the container.

8. A device according to claim 7 wherein the lugs project outwardly from the ring at an angle of 55°–60°.

* * * * *